US005847393A

United States Patent [19]

Van Den Berg et al.

[11] Patent Number: 5,847,393

[45] Date of Patent: *Dec. 8, 1998

[54] CONTROL OF GASEOUS HYDROGEN PEROXIDE CONCENTRATION DURING STERILIZATION

[75] Inventors: Rian Van Den Berg, Sliedrecht, Netherlands; Mark S. Zetter; Keith L. Miller, both of El Dorado Hills, Calif.; Terry R. Todd, Placerville, Calif.

[73] Assignee: UOP, Des Plaines, Ill.

[ * ] Notice: The term of this patent shall not extend beyond the expiration date of Pat. No. 5,600,142.

[21] Appl. No.: 759,994

[22] Filed: Dec. 3, 1996

Related U.S. Application Data

[63] Continuation-in-part of Ser. No. 451,842, May 26, 1995, Pat. No. 5,600,142.

[51] Int. Cl.[6] .................... G01N 21/35

[52] U.S. Cl. .................... 250/339.13; 250/339.09; 250/343

[58] Field of Search .................... 250/339.09, 339.12, 250/339.13, 343

[56] References Cited

U.S. PATENT DOCUMENTS 4,800,279 1/1989 Hieftje et al. .................. 250/339.12 X
5,532,487 7/1996 Brearley et al. ............... 250/339.09 X
5,600,142 2/1997 Van Den Berg et al. .......... 250/343 X

FOREIGN PATENT DOCUMENTS 5-281138 10/1993 Japan ................................ 250/339.12

*Primary Examiner*—Edward J. Glick
*Attorney, Agent, or Firm*—Thomas K. McBride; Frank S. Molinaro; Maryann Maas

[57] ABSTRACT

On line and essentially continuous measurements of hydrogen peroxide vapor in the presence of water vapor can be made using near infrared (NIR) spectroscopy using fiber optic cables to transmit infrared radiation between, e.g, a sterilization chamber and the NIR instrument. Measurement of hydrogen peroxide concentration in the foregoing manner is incorporated into a control system which automatically adds gaseous hydrogen peroxide to the sterilization chamber when the measured concentration falls below a precalculated value. Such a control system ensures the presence in the sterilization chamber of an adequate concentration of gaseous hydrogen peroxide to effect sterilization throughout the sterilization procedure.

8 Claims, 1 Drawing Sheet

CONTROL OF GASEOUS HYDROGEN PEROXIDE CONCENTRATION DURING STERILIZATION

CROSS REFERENCE TO RELATED APPLICATION

This application is a continuation-in-part of application Ser. No. 08/451842, filed May 26, 1995, now U.S. Pat. No. 5,600,142, all of which is incorporated by reference.

BACKGROUND OF THE INVENTION

This invention relates to the control of gaseous hydrogen peroxide concentration, which is made possible by quantitative analysis of hydrogen peroxide in the vapor phase, whether at ambient, reduced, or elevated pressure. More particularly, this invention relates to on-line near infrared spectroscopic analysis of vaporized hydrogen peroxide in sterilization procedures where vaporized hydrogen peroxide must be determined in the presence of water and sometimes in the presence of diverse organic vapors, and use of the measured concentration to ensure a concentration of $H_2O_2$ effective for sterilization throughout the procedure.

Sterilization methods are used in a broad range of applications and have used an equally broad range of sterilization agents. By "sterilization" we refer to the complete destruction or irreversible inactivation of all microorganisms, especially on inanimate objects. The term "disinfectant" appears to be narrower in that it is directed only against organisms considered harmful. Consequently the term "sterilization" includes the use of disinfectants applied to inanimate objects. Among the traditional methods of sterilization are included heat sterilization, most commonly via steam, and chemical sterilization using a variety of agents including alcohols, aldehydes such as formaldehyde, phenols, ozone, and ethylene oxide. Chemical sterilization usually is referred to as cold sterilization for obvious reasons. Each of the methods has its own disadvantages. The major disadvantage of heat sterilization is that some objects to be sterilized can not physically withstand the necessary heat treatment, especially where the objects are polymers or delicate instruments subject to thermal degradation or damage. Various chemical sterilization agents actually react with one or more of the materials of construction of the sterilization objects, hence also must be used with caution. Chemical sterilization agents also suffer from the disadvantage that they may pose disposal or human toxicity problems, requiring extraordinary handling and/or safety procedures.

Hydrogen peroxide and peracids are powerful antimicrobial agents and effective sporicides. A 35 weight percent solution of hydrogen peroxide can be stored for prolonged periods, is easy to handle, is non-corrosive, and mixes readily with water. An important advantage of hydrogen peroxide in sterilization is that it decomposes to oxygen and water, thus presenting no disposal problems.

The use of hydrogen peroxide as a vapor in sterilization also brings along related problems and needs. As with other sterilization agents the effectiveness of hydrogen peroxide under a given set of conditions depends upon its concentration. Therefore, it is not merely important but even critical to have a rapid, accurate method for monitoring hydrogen peroxide concentration in the vapor state in order to ensure effective sterilization. Since hydrogen peroxide always is accompanied by water, a suitable measurement must be capable of selectively monitoring hydrogen peroxide concentrations in the presence of water vapor, and usually in the presence of water vapor at concentrations somewhat higher than those of hydrogen peroxide. Sterilization by hydrogen peroxide also can be performed under conditions where there is the possibility of a significant concentration of organic vapors. Therefore it is important to measure the concentration of hydrogen peroxide in the presence of organic vapors as well as to independently alert the operator to the presence of organic vapors which otherwise could invalidate the hydrogen peroxide measurements, especially by the methods described within.

Hydrogen peroxide also poses occupational health and safety issues, thus it is important to know with confidence that when sterilization is complete residual peroxide remaining after excess hydrogen peroxide decomposition is sufficiently low as to be safe. In humans, brief contact of hydrogen peroxide with the skin leads to irritation and whitening (cutaneous emphysema), the severity of which depends on concentration. Longer contact or higher concentration can lead to burns. Contact with the eyes also leads to serious injuries. Hydrogen peroxide vapor or aerosol causes irritation or damage of the upper respiratory tract and serious lung injuries. The threshold concentration for acute irritative effects of vaporized hydrogen peroxide on the respiratory tract is about 10 $mg/m^3$ in humans; the corresponding value for skin is 20 $mg/m^3$ for humans.

It also is desirable that measurements be made in real time and remotely. That is, it is desirable that the measurement process can be completed in a relatively short time, so that one can monitor the hydrogen peroxide concentration as the sterilization process proceeds. Additionally, it is desirable that measurements be done without bringing samples to the measuring instrument but instead have the measuring instrument located remotely from the sterilization chamber while monitoring $H_2O_2$ in situ. Both of the latter requisites are fulfilled using near infrared spectroscopy with optical fiber cables carrying electromagnetic radiation between the sample and the instrument with probes inserted directly into the sterilization chamber to sample hydrogen peroxide. In the context of this application a "probe" is that portion of the measuring system which brings electromagnetic radiation to the sample, which provides means for transmitting the radiation across the sample path, and which provides means for returning the transmitted radiation to the instrument for further processing. In brief, a probe contains the means necessary to allow a portion of the near infrared spectrum to be absorbed by the sample. In a variant the chamber itself can be used as a probe by mounting light senders and receivers on either side of the chamber with optical fibers carrying light to and from optical measuring instrumentation. It also is significant to note that the radiation used in the method is at such an extremely low level as to have no effect on people or products, and the method presents no fire or explosion hazard.

Our invention satisfies all of the foregoing criteria. That is, our invention accurately measures gaseous hydrogen peroxide concentrations in the presence of water vapor, measurements can be done quickly, virtually continuously, and the measuring apparatus can be located remotely vis-a-vis the sterilization chamber. In particular, the absorbance in the near infrared spectrum of hydrogen peroxide is determined at a frequency or narrow band of frequencies, and alternatively over a much broader wavelength range, where hydrogen peroxide is known to absorb in the near infrared. The concentration of water is concurrently determined from absorbance measurement at other frequencies, or via some correlation function to a spectrum measured over a broader wavelength as stated above. Measurements may be performed in vacuo, at ambient pressure, or above ambient pressure, according to how sterilization is conducted. Incorporation of the on-line measurement of hydrogen peroxide vapors during the course of the sterilization procedure into a control process, where the gaseous hydrogen peroxide concentration is adjusted to ensure a sterilization-effective concentration of $H_2O_2$ at all times at the sterilization conditions extant, is the principal subject matter of this application.

SUMMARY OF THE INVENTION

The purpose of our invention is to perfect a method for controlling hydrogen peroxide vapor under sterilization conditions using near infrared spectroscopy as the technique for monitoring hydrogen peroxide vapor concentration. An embodiment incorporates measuring absorbance in the near infrared at approximately 1420 nanometers, measuring the absorbance in the 1350–1400, and/or 1830–2000, and/or 915–950 nanometer range to determine water concentration, subtracting from the absorbance at 1420 the contribution of water to said absorbance, determining the concentration of hydrogen peroxide from the residual absorbance at 1420 using Beer's law, and applying the measured concentration to control the incremental vaporization of hydrogen peroxide. In another embodiment the presence of organic vapors is detected and measured in the 900–980 and/or 1090–1290 and/or 1550–1800 nanometer region with the absorbance in the 1420 nanometer region thereafter corrected for the calculated contribution from organic vapors. In yet another embodiment the near infrared spectrum is measured over a broad band of the infrared within the region of 900–2000 nanometers with analogous information obtained by applying a multivariant statistical technique to the measured spectrum in order to extract the requisite hydrogen peroxide concentration, and thereafter using the measured concentration in a loop which controls the incremental vaporization of hydrogen peroxide. Other embodiments will be apparent from the ensuing description.

DESCRIPTION OF THE INVENTION

Figure 1:
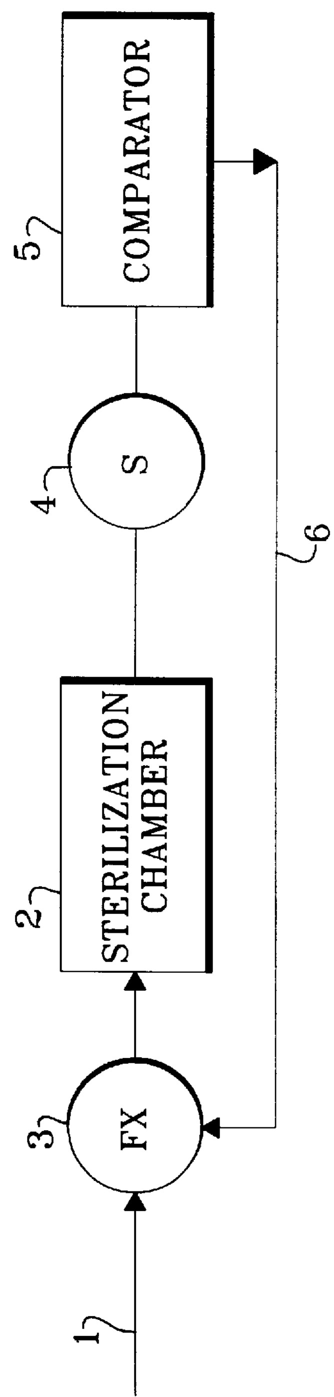
FIG. 1 illustrates a process for on-line control of the concentration of $H_2O_2$ vapors using near infrared spectroscopy as the monitoring method.

There is a need to rapidly measure hydrogen peroxide vapor concentration in the presence of water vapor, especially in real time during sterilization procedures, and especially to ensure a sterilization-effective concentration of hydrogen peroxide vapor—i.e., at least the minimum concentration effective for sterilization—at all times during the sterilization procedure. This need can be satisfied by the method described herein based on near infrared spectroscopy, which also has the desirable feature that instrumentation can be located remotely from the sample since the pertinent light frequencies can be transmitted readily over optical fibers. Our invention is based on the observation that hydrogen peroxide vapor has a strong absorption in the near infrared centered at approximately 1420 nanometers. The contribution to the absorbance at 1420 nm from water can be calculated by measuring the water absorbance in one or more of the 1350–1400, the 1830–2000, and 915–950 nm regions where hydrogen peroxide is essentially transparent. From the known relation between water vapor absorbance in the latter two regions and its absorbance at 1420 nm one can calculate the contribution from water vapor to the 1420 absorbance to arrive at an absorbance arising solely from hydrogen peroxide. It then becomes a simple matter to apply Beer's law to calculate hydrogen peroxide concentration.

The samples which are being measured in the practice of our invention generally are gaseous samples, or head space, in sterilization chambers using hydrogen peroxide as a sterilizing agent. Since hydrogen peroxide always decomposes to form water and vapors are normally generated from aqueous hydrogen peroxide, the gaseous samples being analyzed always are at least a mixture of hydrogen peroxide and water. In addition, the samples can contain organic vapors from, e.g., outgassing, previous washes in organic solvents, and so forth, a fact which has implications both in validation of the hydrogen peroxide concentration measurements as well as in modifications of the hydrogen peroxide measurement which are elaborated upon within.

The absorbance of the vapor is measured at about 1420 nm, which is roughly the mid-point of an absorption band of hydrogen peroxide. However, since water and many organic vapors also absorb at this wavelength there is a need to correct the measured absorbance for the presence of interfering components. In general, the measured absorbance may be thought of as the sum of several absorbances, $$A_{1420}(\text{total})=A_{1420}(H_2O_2)+A_{1420}(H_2O)+A_{1420}(\text{organics})$$

As the foregoing clearly shows it is necessary to subtract the absorbances arising from water and organic vapors in order to correctly ascertain the absorbance associated solely with hydrogen peroxide.

The corrections associated with water absorptions may be applied by measuring the absorbance at at least one wavelength within at least one of the regions 1350–1400, 1830–2000, and 915–950 nm, regions where hydrogen peroxide is transparent (i.e., there is no absorption by hydrogen peroxide in these regions). As stated above, the absorbance must be measured at at least one wavelength in one of the foregoing regions; which region is chosen is a matter of choice. It also is possible to make more than one measurement in any or all of the foregoing regions. Additionally, one has the choice of making absorbance measurements either at one or a multiplicity of discrete wavelengths or measuring an integrated absorbance over some band of wavelengths within the stated region. Whichever variant is chosen the concentration of water then may be calculated from the measured absorbance, using the appropriate extinction coefficient at measured wavelengths where discrete absorbances are measured or using an integrated extinction coefficient where an integrated absorbance is measured. In either case one calculates the absorbance at 1420 nm arising from the concentration of water as measured in the foregoing description using the water concentration as measured above and the known extinction coefficient of water at 1420 nm. The calculated contribution of water is then subtracted from the measured absorbance at 1420 to give a corrected absorbance which, except for the possible contributions from organic vapors, represents the absorbance of hydrogen peroxide alone.

Where the absorbance of organic vapors at 1420 is small relative to the total absorbance at that wavelength, then $$A_{1420}(\text{total})=A_{1420}(H_2O_2)+A_{1420}(H_2O)$$

Rearranging, $$A_{1420}(H_2O_2)=A_{1420}(\text{total})-A_{1420}(H_2O)$$

It then is a simple matter to calculate the concentration of hydrogen peroxide from its absorbance using Beer's law which states A=elc, where e is the extinction coefficient of a substance at the measured wavelength, l is the sample path length, and c is the concentration of the substance being measured in the sample. As an example of making absorbance corrections, we have noted that the absorbance of water at 1420 nm is ca. ⅙that of the absorbance at 1360 nm. Therefore, by measuring the absorbance at 1360 nm one can readily correct for water absorbance in the 1420 nm region.

It is possible to simplify the foregoing even more where the contribution of water vapor to the absorbance at 1420 nm is small, or where one needs only an approximate measurement of hydrogen peroxide concentration, by ascribing all of the absorbance in the 1420 nm region to hydrogen peroxide. Clearly this is inaccurate, yet for some purposes the results are adequate.

As stated above, there are possible interferences to the hydrogen peroxide measurement if other vapors are present that absorb radiation at about 1420 nm. Practically all organic materials absorb in this region, consequently organic solvent vapors generally will interfere with the measurement as described above. However, such materials also absorb in other areas of the near infrared, particularly in the regions 900–980, 1090–1290 nm, 1550–1800 nm, and 2100–2400 nm where neither hydrogen peroxide nor water absorb. Thus, if interfering organic vapors are present they can be detected, independently of hydrogen peroxide and water vapors, by NIR measurements in these other regions either to give warning that the hydrogen peroxide measurement is not valid or to make approximate corrections to the absorbance at 1420 nm. General relationships do exist between the intensities of the organic vapor peaks in the 1090–1290 or 1550–1800 nm regions and those in the 1420 region, with a typical ratio of absorbance at any particular peak maximum to that at 1420 nm being in the range of 1.5:1 to 1:1. Thus, approximate, non-specific corrections could be made to the hydrogen peroxide value based on absorbances in non-hydrogen peroxide active regions. Of course, if the interfering substances are known more precise corrections could be made in the same manner as described for water above.

In any optical system the system reference must be established regularly, i.e., the system optical performance must be measured at regular intervals with no active sample, or other absorbing material that is subject to change, in the optical beam path. This establishes a baseline performance such that signals generated in the presence of a sample are then directly related only to the sample and not to changes in the optical system. The difficulty presented by system reference procedures for the hydrogen peroxide concentration measurements is that water vapor is generally naturally present in the optical path at a concentration comparable to that generated during hydrogen peroxide sterilization. Where measurement of water vapor itself is unimportant the foregoing difficulty has no practical effect. However, because no reference can be easily established in ambient air, more elaborate reference procedures need to be devised where the measurement of water vapor also is required.

Where sterilization by hydrogen peroxide is performed under vacuum the first step after sealing the vacuum chamber is to evacuate it to a pressure of 20 torr or less. This removes essentially all the water vapor (740/760-ths, or 97%, is removed) and a reference spectrum can be taken, preferably automatically, after evacuation and prior to addition of hydrogen peroxide to the evacuated system.

Where sterilization is not done in vacuo, establishing a reference is somewhat more inconvenient. One method would be to insert into the entire sample path used for peroxide measurement a reference sample of a sealed tube with optical windows at each end containing dry air, or evacuated to a degree that the water vapor concentration is negligible. After the reference spectrum is obtained the reference sample is replaced and the hydrogen peroxide measurement obtained.

Other methods of establishing a reference can be envisaged. What is critical is that a reference procedure be established. However, the particular method used is not a critical part of our invention as described herein, and which method ultimately is applied is one of choice for the skilled worker.

Related to the need for periodically establishing a system reference is the need to periodically validate or calibrate the system performance. Simplistically, this is accomplished by placing in the normal sample path a calibration sample, i.e., a sample containing known concentrations of vaporized hydrogen peroxide, water, and perhaps organic vapors. If the concentrations calculated from the measured absorbances do not afford values for the analyte concentrations with sufficient accuracy, this indicates that the measuring procedure is faulty, such as may arise from faulty referencing, changing system performance, and faulty procedures. The difficulty of the foregoing procedure may be attributed to the difficulty of providing samples with accurately determined and stable concentrations of the analytes. So, for example, because of the relative instability of hydrogen peroxide it is challenging to prepare a sample with known concentrations of hydrogen peroxide vapor which do not appreciably change even over relatively short periods of time, especially in the presence of readily oxidizable organic materials.

The foregoing descriptions of hydrogen peroxide concentration determinations were couched in terms of making discrete measurements at particular wavelengths, but analogous procedures utilizing measurements made over one or more bands of wavelengths within the region from about 900 to about 2000 nm often are advantageous and preferred. The region within which the band or bands of measurement are taken is critical; the region 900–2000 nm encompasses the principal hydrogen peroxide absorbtion maximum at about 1420 nm as well as the water vapor absorbtion maxima at 915–950 nm, 1350–1400 nm, and 1830–2000 nm. In particular, one may measure the near infrared spectrum of a series of samples containing known concentrations of hydrogen peroxide and water vapor over the entire region from 900–2000 nm, over one continuous region within 900–2000 nm but yet not spanning the entire region, or over a combination of smaller, more discrete bands within the stated region, so long as measurements include the $H_2O_2$ absorbtion band in the 1420 nm region, and at least one of the water absorbtion bands at 915–950, 1350–1400, and 1830–2000 nm. One then can obtain a correlation between the measured spectra and the known concentrations of the components in the calibration set being used by applying a multivariant statistical technique, such as partial least squares, principal component regression, and so forth. Whatever statistical technique is used effectively determines the best wavelength regions within which to make measurements and the relative weights of the components of the measurement. One next measures the near infrared spectrum of an unknown sample over the same region where the statistical correlation has been obtained for the calibration set and applies the same multivariant statistical technique to the measured near infrared spectrum of the unknown sample to calculate the concentration of hydrogen peroxide vapor therein.

For sterilization with hydrogen peroxide to be effective, the concentration of gaseous hydrogen peroxide must be at some minimum precalculated level. Hydrogen peroxide will react with many surfaces undergoing sterilization, and also will permeate into and through plastic materials. Both of the foregoing can cause hydrogen peroxide levels in a sterilization chamber to be lower than expected leading to rapid loss of peroxide vapor with the possibility of its concentration decreasing to less than sterilization levels. The result of an uncertain hydrogen peroxide vapor concentration with the attending possibility of imperfect or incomplete sterilization clearly is not an acceptable one. Consequently there is a need of controlling hydrogen peroxide vapor concentration using in situ real time measurements to ensure at least the minimum amount of hydrogen peroxide necessary to effect sterilization throughout the duration of the sterilization procedure. The foregoing NIR method of hydrogen peroxide measurement can be readily incorporated into a control process to ensure adequate (i.e., sterilization-effective) vapor state concentrations throughout the sterilization procedure.

For example, the measurements may be performed on-line virtually continually, or at least with such frequency as to be operationally tantamount to continual measurements. An ancillary software program used to determine hydrogen peroxide concentration in the manner described above also can generate as output a signal proportional to hydrogen peroxide concentration with the signal being used as input by a hydrogen peroxide vapor generating device. The difference between the signal received by the hydrogen peroxide vapor generating device and a "setpoint" signal, i.e., some reference signal, then serves to generate additional hydrogen peroxide vapor until the aforementioned difference is zero. In essence the control system comprises a monitoring device (here an NIR spectrometer) whose electronic output is representative of actual hydrogen peroxide concentration, a controller which reads the monitor's electronic output and translates the difference between the actual and desired (or setpoint) hydrogen peroxide vapor levels into a signal, generally a second electronic signal, which is transmitted to the hydrogen peroxide generating device to produce more hydrogen peroxide. The foregoing control process is schematically illustrated by FIG. 1. Gaseous hydrogen peroxide enters through line 1 into the sterilization chamber 2 through controller 3. The controller varies the amount of vaporized hydrogen peroxide entering 2 by, e.g., controlling the extent of vaporization from an aqueous solution of hydrogen peroxide. Sensor 4 receives a signal from chamber 2 which is proportional to the vaporized hydrogen peroxide concentration and transmits it to a comparator 5, where the signal is compared to a setpoint or reference signal representing the desired hydrogen peroxide concentration. The difference between signals is translated into an electronic signal 6 transmitted by 5 to the controller 3 which determines the amount of vaporized hydrogen peroxide entering chamber 2, thereby maintaining the peroxide concentration within the chamber at the desired level. It needs to be explicitly understood that the "desired level" of gaseous hydrogen peroxide is precalculated and is a concentration effective to bring about sterilization within the sterilization conditions (temperature, time, degree of contact, etc.) which are used. It also needs to be explicitly understood that our method of controlling hydrogen peroxide will be applied through the duration of sterilization; clearly a sterilization-effective concentration of gaseous hydrogen peroxide is required for the entire sterilization time cycle.

The above descriptions were couched in terms of making discrete measurements at particular wavelengths. Analogous procedures may be based upon measurements over one or more bands of wavelengths within the region from about 900 to about 2000 nm. The region within which the band or bands of measurement are taken is critical; the region 900–2000 nm encompasses the principal hydrogen peroxide absorption maximum at about 1420 nm as well as the water vapor absorption maxima at 915–950 nm, 1350–1400 nm, and 1830–2000 nm. In particular, one may measure the near infrared spectrum of a series of samples (a calibration set) containing known concentrations of hydrogen peroxide and water vapor in various combinations within the stated region. One then can obtain a correlation between the measured spectrum and the known concentrations of the components in the calibration set being used by applying a multivariant statistical technique, such as partial least squares, principal component regression, and so forth. Whatever statistical technique is used effectively determines the best wavelength regions within which to make measurements and the relative weights of the components of the measurement. One then can measure the near infrared spectrum of an unknown sample over the same region where the statistical correlation has been obtained and using a multivariant statistical technique applied to the measured near infrared spectrum of the unknown sample one can calculate the concentration of hydrogen peroxide vapor therein. This approach is merely an extension of the one described earlier; the difference is that statistical techniques are applied to a measured near infrared spectrum over a band of frequencies rather than using either absorbances at discrete frequencies, or integrated absorbances over a narrow range of frequencies. We also note that whereas statistical techniques have been applied to near infrared spectra of samples to determine physical properties (e.g., octane number, Reid vapor pressure, and so forth) of the sample this approach does not seem to have been successfully extended to the determination of the chemical composition of a sample, i.e., analyte concentration. Thus, this variant of our invention represents a hitherto unknown—but manifestly significant—extension of familiar statistical techniques as applied to near infrared spectra into the unfamiliar domain of chemical analysis and its subsequent utilization in a control process. Since success was by no means certain our invention represents a significant departure from the prior art.

What is claimed is:

1. A method of continuously controlling the concentration of gaseous hydrogen peroxide in a sterilization chamber to provide at least a precalculated concentration of said gaseous hydrogen peroxide comprising:

a. measuring the concentration of gaseous hydrogen peroxide in the sterilization chamber by
   i. measuring a first absorbance of a gaseous sample at a wavelength in a first region at approximately 1420 nanometers and at least one second absorbance at at least one wavelength selected from at least one second region at 915–950, 1350–1400 and 1830–2000 nanometers;
   ii. subtracting from the first absorbance an amount arising from water vapor as calculated from the measured second absorbance in the second region to afford a third absorbance at approximately 1420 nanometers corrected for water vapor; and
   iii. determining the concentration of gaseous hydrogen peroxide from said third absorbance using Beers Law to afford a measured concentration of gaseous hydrogen peroxide;
b. comparing the measured concentration of gaseous hydrogen peroxide with said precalculated concentration; and c. automatically adding additional gaseous hydrogen peroxide to the sterilization chamber when said measured concentration of gaseous hydrogen peroxide is less than said precalculated concentration.

2. The method of claim 1 where steps a–c are repetitively applied during the duration of sterilization.

3. A method of continuously controlling the concentration of gaseous hydrogen peroxide in a sterilization chamber to provide at least a precalculated concentration of said gaseous hydrogen peroxide comprising:

a) measuring the concentration of gaseous hydrogen peroxide in the sterilization chamber by i. obtaining the near infrared spectrum of a series of calibration samples containing known concentrations of hydrogen peroxide vapor, water vapor, and combinations thereof over the region from about 900 to about 2000 nanometers;

ii. establishing a correlation between the series of near infrared spectra of said calibration samples obtained in part i. and the known concentrations of gaseous hydrogen peroxide in said calibration samples using a multivariant statistical technique;

iii. obtaining the near infrared spectrum of a gaseous sample from the sterilization chamber over the said region of part i.; and iv. applying the multivariant statistical technique to the near infrared spectrum of the gaseous sample to calculate the concentration of gaseous hydrogen peroxide therein, thereby affording a measured concentration of gaseous hydrogen peroxide;

b) comparing the measured concentration of gaseous hydrogen peroxide with said precalculated concentration; and c) automatically adding additional gaseous hydrogen peroxide to the sterilization chamber when said measured concentration of gaseous hydrogen peroxide is less than said precalculated concentration.

4. The method of claim 3 where steps a–c are repetitively applied during duration of sterilization.

5. The method of claim 3 where said region of part a) i. includes about 1420 nm and at least one of the intervals 915–950 nm, 1350–1400 nm, and 1830–2000 nm.

6. The method of claim 5 where said region includes 915–950 nm.

7. The method of claim 5 where said region includes 1350–1400 nm.

8. The method of claim 5 where said region includes 1830–2000 nm.

* * * * *